United States Patent [19]

Tamura et al.

[11] 4,456,562
[45] Jun. 26, 1984

[54] PROCESS FOR PRODUCING NITRILES

[75] Inventors: Mitsuhisa Tamura; Hiroshi Sato, both of Ibaraki, Japan

[73] Assignee: Sumitomo Chemical Company, Limited, Osaka, Japan

[21] Appl. No.: 444,046

[22] Filed: Nov. 23, 1982

[30] Foreign Application Priority Data

Dec. 2, 1981 [JP] Japan .................. 56-194128
Apr. 2, 1982 [JP] Japan .................. 57-55741

[51] Int. Cl.³ .................................... C07C 120/00
[52] U.S. Cl. .................. 260/465 F; 260/464; 260/465 D; 260/465 G; 260/465 H; 260/465 R; 260/465.1; 260/465.9
[58] Field of Search ........... 260/465 R, 465 D, 465 F, 260/465 G, 465 H, 465.1, 465.9

[56] References Cited

U.S. PATENT DOCUMENTS 3,225,081 12/1965 Koopman et al. .............. 260/465 G
4,235,807 11/1980 Fuhlhage ...................... 260/465 G

OTHER PUBLICATIONS

SYNTHESIS, Feb. 1979, pp. 112–113, G. A. Olah et al., "Synthetic Methods and Reactions; 60. Improved One-Step Conversion of Aldehydes into Nitriles with Hydroxylamine in Formic Acid Solution".

Primary Examiner—Dolph H. Torrence
Attorney, Agent, or Firm—Stevens, Davis, Miller & Mosher

[57] ABSTRACT

In a process for producing a nitrile compound from a corresponding aldehyde exhibited by the general formula (I) and a hydroxylamine inorganic acid salt $$R^1CHO \qquad (I)$$

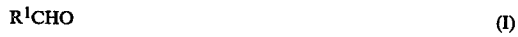

or from an aldoxime exhibited by the general formula (II), $$R^2CH=NOH \qquad (II)$$

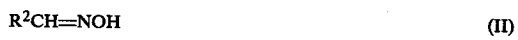

(in the general formulas shown hereinabove, $R^1$ represents an aryl group having 6 to 9 carbon atoms and $R^2$ represents an alkyl or alkenyl group having 1 to 9 carbon atoms or an aryl group having 6 to 9 carbon atoms), a process, wherein water produced in the reaction is azeotropically distilled out of the reaction system with the aid of a solvent which makes an azeotropic mixture with water.

The nitrile compound is useful as an important intermediate for the synthesis of pharmaceuticals or pesticides.

7 Claims, No Drawings

PROCESS FOR PRODUCING NITRILES

The present invention pertains to an improved process for producing nitrile compounds, more particularly it relates to an improved process for producing a nitrile compound (III) from a corresponding aldehyde exhibited by the general formula (I) and a hydroxylamine inorganic acid salt (referred to as "hydroxylamine salt" hereinafter),

$$R^1CHO \quad (I)$$

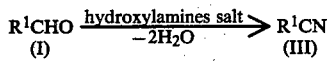

$$R^1CHO \xrightarrow[-2H_2O]{\text{hydroxylamines salt}} R^1CN$$
$$(I) \quad\quad\quad\quad\quad\quad\quad (III)$$

or from an aldoxime exhibited by the general formula (II),

$$R^2CH=NOH \quad (II)$$

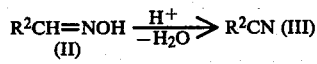

$$R^2CH=NOH \xrightarrow[-H_2O]{H^+} R^2CN \text{ (III)}$$
$$(II)$$

(In general formulas shown hereinabove, $R^1$ represents an aryl group having 6 to 9 carbon atoms and $R^2$ represents an alkyl or alkenyl group having 1 to 9 carbon atoms or an aryl group having 6 to 9 carbon atoms, wherein said organic groups may be substituted by one or more of cyano, hydroxyl, alkoxyl, nitro, alkoxycarbonyl, amido group, halogen atom or any group containing unsaturated bond such as allyl group).

Objective nitrile compounds of the present invention are important intermediate compounds used as raw materials for the synthesis of pharmaceuticals or pesticides. For example, p-cyanophenol, one of the objective compounds of the present invention, is known as an important intermediate utilized for the synthesis of pesticides such as Cyanox ® (Resistered Trade Name of Sumitomo Chemical Co., Ltd.) (o,o-dimethyl-o,p-cyanophenylphosphorothioate), Bromoxynil (4-cyano-2,6-dibromophenol) and the like.

As for processes producing a nitrile compound, from an aldehyde and a hydroxylamine salt or from an aldoxime, there are known many processes. Representative processes are such that, in one process an oxime compound is first synthesized from an aldehyde and a hydroxylamine salt and after being isolated, said oxime compound is dehydrated in the presence of a dehydrating agent to produce a nitrile compound (referred to as "Two step method", hereinafter) and in other process a nitrile compound is directly produced by dehydration from an aldehyde and a hydroxylamine salt without isolation of an oxime compound (referred to as "One step method", hereinafter).

In Two step method, a nitrile compound is well known to be prepared by the dehydration of a corresponding aldoximes in the presence of a dehydrating agent. As for the dehydrating agent, there is exemplified phosgene, thionyl chloride, phosphorus chloride, orthoester, dicyclohexylcarbodiimide, trifluoroacetic anhydride [Shin Jikken Kagaku Koza, published by Maruzen Co., Ltd., Vol. 14III, 1466; J. Org. Chem., 39, 3424 (1974); Chem. Ber., 107, 1221 (1974) and Tetrahedron Lett., (1976) 603]. In said process, a dehydrating agent must be used in the stoichiometric amount or more to aldoxime and can not be recovered so that this process is not deemed to be economically sufficient from an industrial viewpoint. There was developed lately another modification in said process utilizing selenium dioxide as a catalyst in synthesizing a nitrile compound from an aldoxime. (G. Sosnovsky; Synthesis, 1978, 703) However, selenium dioxide is known to be highly toxic and it is not advantageous to use a toxic substance in an industrial process and therefore this modification is not sufficient to be conducted as a commercial process.

One step method wherein a nitrile compound is obtained directly from a corresponding aldehyde has much merit such as simplicity in a process compared with Two step method wherein an aldoxime intermediate is once isolated on the way synthesizing a nitrile compound from the aldehyde. As for One step method there are also known various kinds of variation, as disclosed in Ger. Offen. 2,014,984; Synthesis, (1979) 722; Chem. Ber., 107, 1221 (1974); Synthesis, (1981) 739; Japanese Patent Publication (Unexamined) No. 169,664/1981; Helv. Chim. Acta, 59, 2786 (1976). However, these processes cannot be satisfactory from an industrial viewpoint, because for example, formic acid, a highly corrosive chemical is used in a large amount or selenium dioxide, a highly toxic compound is used as a catalyst, a specific hydroxylamine derivative which is industrially not easily obtained is used as a reactant, or an expensive dehydrating agent must be used in the stoichiometric amount or more to the aldehyde.

In order to solve the aforesaid various problems of the method so far, the present inventors have intensively studied to provide an improved process for producing nitrile compounds in both One step and Two step methods. Eventually, it has been found that firstly in Two step method dehydration of an aldoxime proceeds by an acid catalyst, secondly the reaction proceeds easily by azeotropically distilling the water produced in the reaction out of the reaction system, as specifically explaining in embodiment, and in One step method, a nitrile compound can be easily obtained by only mixing an aldehyde and a hydroxylamine salt under heating.

One general object of the present invention is to provide an improved process for producing nitrile compounds. A further object is to provide an improved process for producing a nitrile compound from a corresponding aldehyde and a hydroxylamine salt (One step method) or from an aldoxime (Two step method). These and other objects and advantages of the invention will be apparent to persons skilled in the art from the following description.

Thus, in Two step method for producing a nitrile compound from a corresponding aldoxime, it was found that the dehydration reaction could be conducted in a constant high yield of a nitrile compound in the presence of a catalytic amount of an acid, when the water produced in the reaction is immediately removed by the azeotropic distillation. Furthermore, selectivity for a nitrile compound is increased when a small amount of an amide compound is added in the reaction system. Moreover, it is a great surprise that when formamide is used as an amide, formamide itself serves as a catalyst and the dehydration reaction proceeds rapidly in the absence of any acid catalyst and an objective nitrile compound can be obtained in a high yield.

In One step method for producing a nitrile compound from a corresponding aldehyde and a hydroxylamine salt, dehydration can be accomplished without addition of any catalyst or dehydrating agent when the water produced in the reaction is removed immediately by the azeotropic distillation. Furthermore, when a small amount of an amide is added in a reaction system, selectivity for a nitrile compound improves and thereby an objective nitrile compound can be obtained in a high yield. It cannot be expected in advance azeotropic dehydration and addition of an amide serve for the reaction effectively even in the case of One step method. A big difference between One and Two step methods is in that acid catalyst is essential in Two step method and on the contrary it is not necessary in One step method.

The reason why amide compounds are effective for the selectivity enhancement is also not so clear, but can be inferred hereinafter. That is to say, amide compounds may have efficiency in controlling acid strength of an acid catalyst (one reason) and in controlling solubility between aqueous layer and hydrocarbon layer (the other reason). When, for example, hydroxylamine hydrochloride is used as a hydroxylamine salt, a nitrile compound can be obtained in a good selectivity without addition of an amide, because presumably acid strength of hydrochloric acid separated as the reaction proceeds is comparatively moderate or a part of it gets out of reaction system. However, when hydroxylamine sulfate is used, selectivity for a nitrile compound somewhat decreases, because presumably acid strength of sulfuric acid separated is strong. One of the reason why addition effect of an amide is especially predominant when hydroxylamine sulfate is used is inferred to reside in neutralization effect of an amide to sulfuric acid. Furthermore, when aqueous solution of hydroxylamine sulfate is used, the reaction system comprises two layers wherein the upper layer is hydrocarbon or halogenated hydrocarbon layer (an aldehyde is distributed to both layers) and an amide can be inferred to contribute to the enhancement of contact effectiveness between both layers.

An arylaldehyde exhibited by the general formula (I) used as a starting material in One step method in the present invention is exemplified by (o-, m-, p-)hydroxybenzaldehyde, (o-, m-, p-)nitrobenzaldehyde, (o-, m-, p-)cyanobenzaldehyde, (o-, m-, p-)methoxybenzaldehyde, (o-, m-, p-)acetoxybenzaldehyde, (o-, m-, p-)benzaldehydecarboxamide, (o-, m-, p-)N,N-dimethylbenzaldehydecarboxamide, (o-, m-, p-)chlorobenzaldehyde, (2,4-, 2,5-, 2,6-, 3,4-)dichlorobenzaldehyde, (o-, m-, p-)bromobenzaldehyde, (2,4-, 2,5-, 2,6-, 3,4-)dibromobenzaldehyde or substituted benzaldehydes having two or more kinds of substituents hereinabove. An aldehyde which remarkably shows the effect of the present invention is p-hydroxybenzaldehyde.

A hydroxylamine salt used in One step method of the present invention is hydroxylamine sulfate or hydroxylamine hydrochloride.

An oxime used as a starting material in Two step method in the present invention can be easily obtained by the ordinary method from, for example, an aldehyde and a hydroxylamine salt. In embodiments, there is exemplified acetaldoxime, propionaldoxime, butylaldoxime, isobutylaldoxime, pentylaldoxime, hexylaldoxime, heptylaldoxime, octylaldoxime, nonylaldoxime, 2-ethylhexylaldoxime, cyclohexanecarboxaldoxime, 2-hexenylaldoxime, cinnamaldoxime, 3,7-dimethyl-6-octenylaldoxime, 2-furfurylaldoxime, (o-, m-, p-)hydroxybenzaldoxime, (o-, m-, p-)nitrobenzaldoxime, (o-, m-, p-)cyanobenzaldoxime, (o-, m-, p-)methoxybenzaldoxime, (o-, m-, p-)acetoxybenzaldoxime, (o-, m-, p-)benzaldehydecarboxamide oxime, (o-, m-, p-)N,N-dimethylbenzaldehydecarboxamide oxime, (o-, m-, p-)chlorobenzaldoxime, (2,4-, 2,5-, 2,6-, 3,4-)dichlorobenzaldoxime, (o-, m-, p-)bromobenzaldoxime, (2,4-, 2,5-, 2,6-, 3,4-)dibromobenzaldoxime or substituted benzaldoximes having two or more kinds of substituents hereinabove. An aldoxime which remarkably shows the effect of the present invention is p-hydroxybenzaldoxime.

An acid used as a catlayst in Two step method in the invention is exemplified, for example, by sulfuric, hydrochloric, nitric, phosphoric, polyphosphoric, perchloric, oxalic, p-toluenesulfonic, benzenesulfonic, methanesulfonic, trifluoroacetic, trifluoromethansulfonic or formic acid or a strong acid-type ion-exchange resin or the like. These can be used singly or in combination thereof. The amount of acid used is 1-50 mole % to an aldoxime.

An amide used for the enhancement of the selectivity of the reaction in the invention is exemplified by formamide, N-methylformamide, N,N-dimethylformamide, acetamide, N-methylacetamide, N,N-dimethylacetamide, N-methylpyrrolidone, hexamethylphosphoric triamide (referred to as "HMPA" hereinafter) or the like. The amount of an amide used is 0.05-1, preferably 0.1-0.5 parts by volume (ml) per 1 part by weight (g) of an aldoxime in case of Two step method and 0.05-1.5, preferably 0.1-0.75 parts by volume (ml) per 1 part by weight (g) of an aldehyde in case of One step method.

A solvent which makes azeotropic mixture with water used in the invention is exemplified by benzene, toluene, xylene, chlorobenzene, heptane, methyl isobutyl ketone (referred to as "MIBK" hereinafter), ethyl acetate or the like.

Reaction temperature may be azeotropic temperature or above of employed solvent and water, and the range of 60°-150° C. is generally employed.

The reaction is carried out usually under atmospheric pressure, however it can also be practicable under increased or reduced pressure.

A nitrile compound obtained by the method of the present invention can easily be recovered by a per se conventional procedure such as extraction or distillation, and it can further be purified by the well known purification technology hitherto known according to the use of a nitrile compound.

The invention is illustrated in detail by the following examples, but not limited thereto.

EXAMPLE 1

30 Grams of p-hydroxybenzaldehyde, 72 ml of 10%-hydroxylamine sulfate aqueous solution (containing 0.247 mole of hydroxylamine), 15 ml of formamide, and 300 ml of toluene were introduced into a 500 ml 4 necked flask equipped with a Dean-Stark apparatus and the reaction mixture was stirred at 110° C. for 4 hrs. After the reaction finished, 9.2 g of 28%-caustic soda aqueous solution and 25 ml of water were added and mixed, then reaction mixture was separated into 3 layers, wherein 99% of p-cyanophenol produced existed in the upper and medium layers and 1% of it was contained in the aqueous layer. The gaschromatographic analysis of the product was conducted in the condition of [5% PEG 20M, 0.5 m, 190° (4 min)→220° (5 min), 2° C./min] and it was found that the conversion of p-hydroxybenzaldehyde was 100%, yield of p-cyanophenol was 94%, and yield of p-hydroxybenzaldoxime was 0.2%.

EXAMPLE 2

503 Milligrams of p-hydroxybenzaldehyde, 323 mg of hydroxylamine hydrochloride and 10 ml of toluene were introduced to a flask of 50 ml, equipped with a Dean-Stark dehydrating apparatus. The reaction mixture was stirred under reflux for 4 hrs. After the reaction finished, water and MIBK were added to the reaction mixture and mixed, followed by separation into two layers. Aqueous layer was extracted again by MIBK and the extract was combined with toluene layer first separated and subjected to the analysis of the products by gaschromatography [5% PEG 20M, 0.5 m, 190° C. (4 minutes retention)→220° C. (5 minutes retention), 2° C./min]. From the results, it was found that the conversion of p-hydroxybenzaldehyde was 100% and 449 mg (91% yield) of p-cyanophenol and 6.1 mg (1.1% yield) of p-hydroxybenzaldoxime were produced.

EXAMPLE 3

Except that 1.0 g of p-hydroxybenzaldehyde and 768 mg of hydroxylamine sulfate as starting materials and 10 ml of toluene were used and 30 minutes of reaction time was employed, the other procedures were carried out in the same manner as in Example 2. From the results, it was found that the conversion of p-hydroxybenzaldehyde was 100% and yield of p-cyanophenol and p-hydroxybenzaldoxime were 72% and 0%, respectively

EXAMPLES 4–9

Except that 1.0 g of p-hydroxybenzaldehyde, 672 mg of hydroxylamine sulfate and 10 ml of toluene, amides, reaction temperatures and times listed in Table 1 were employed, procedures were carried out in the same manner as in Example 3 and the results as shown in the Table 1 were obtained.

TABLE 1

| | | Reaction Results | | |
|---|---|---|---|---|
| Example | Amide*1 (Amounts*2 of addition) | Temp. (°C.) | Time (hrs.) | Conversion (%) | Yield of Nitriles (%) |
| 4 | FA (0.2) | 120 | 4 | 98 | 89 |
| 5 | FA (0.5) | 100 | 6 | 100 | 94 |
| 6 | MFA (0.5) | 120 | 4 | 100 | 92 |
| 7 | DMF (0.5) | 100 | 6 | 100 | 90 |
| 8 | MAA (0.5) | 120 | 4 | 99 | 84 |
| 9 | HMPA (0.5) | 120 | 4 | 99 | 87 |

Note:
*1Abbreviations shown in Table 1 mean as follows:
FA: formamide
MFA: N—methylformamide
DMF: N,N—dimethylformamide
MAA: N—methylacetamide
HMPA: hexamethyl phosphoric triamide
*2Amount of addition means volume amount (ml) of amides added based on 1 part by weight (g) of p-hydroxybenzaldehyde.

EXAMPLE 10

501 Milligrams of p-nitrobenzaldehyde, 272 mg of hydroxylamine sulfate, 0.1 ml of DMF and 5 ml of toluene were introduced into a flask of 25 ml equipped with same apparatus used in Example 2 and the reaction mixture was refluxed for 6 hrs. When the reaction finished, same post treatment as that in Example 2 was conducted and products produced were subjected to gaschromatographic analysis. From the results, it was found that conversion of p-nitrobenzaldehyde was 88% and yield of p-nitrobenzonitrile was 80%.

EXAMPLE 11

16.4 Milligrams of conc. sulfuric acid was introduced into a flask of 10 ml volume, then 5 ml of toluene and 502 mg of p-anisaldoxime were introduced thereto. A Dean-Stark dehydrating apparatus was attached to the flask and the reaction mixture was refluxed under stirring for 2 hrs. After the reaction finished, the reaction mixture was washed with water and the aqueous layer was subjected to extraction with MIBK. Extract was combined with toluene layer first separated from the aqueous layer and subjected to the determination of the products by gaschromatography.

From the results, it was found that conversion of p-anisaldoxime was 100% and 420 mg (95% yield) of p-anisonitrile and 3.7 mg (0.8% yield) of p-anisaldahyde were produced.

EXAMPLES 12–16

Except that oximes listed in the Table 2 were used instead of p-anisaldoxime, the procedure was carried out in the same manner as in Example 11. The results are shown in Table 2:

TABLE 2

| | | Reaction Results | | |
|---|---|---|---|---|
| Example | Aldoxime | Sulfuric Acid (mole %) | Conversion (%) | Yield of Nitriles (%) |
| 12 | 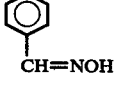 | 5 | 94 | 91 |
| 13 |  | 15 | 100 | 83 |
| 14 | 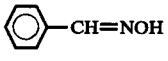 | 6.4 | 100 | 85 |
| 15 | 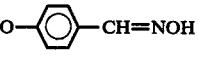 | 14 | 100 | 79 |
| 16 | n-C$_8$H$_{17}$CH=NOH | 15 | 99 | 74 |

EXAMPLE 17

To a 30 ml of flask equipped with distillating apparatus, 30 mg of conc. sulfuric acid, 10 ml of MIBK, 598 mg of p-hydroxybenzaldoxime were introduced and the reaction mixture was heated up to 130° C. Heating under stirring with a magnetic stirrer was continued for 30 minutes, and about 3.5 ml of MIBK thereby was distilled off. Reaction solution was subjected to gaschromatography analysis to find that 392 mg (76% yield) of p-cyanophenol was produced. The conversion was 100%.

EXAMPLES 18–21

Experiments were carried out by using p-hydroxybenzaldoxime as a starting material, various catalysts and solvents. Reaction conditions and the results were as shown in Table 3, wherein reaction temperature was reflux temperature of the solvent used.

TABLE 3

| Example | Catalyst*1 | Amount*2 of Catalyst | Solvent | Time (hrs.) | Conversion (%) | Yield (%) |
|---|---|---|---|---|---|---|
| 18 | $H_2SO_4$ | 14 mole % | Chlorobenzene | ½ | 100 | 75 |
| 19 | p-TsOH | 14 mole % | MIBK | 1 | 100 | 71 |
| 20 | PPA | 10 wt % | Chlorobenzene | 5 | 99 | 70 |
| 21 | HCl gas | 30 mole % | Toluene | ½ | 91 | 71 |

Note:
*1Abbreviations shown in the Table 3 mean as follows:
p-TsOH: p-toluenesulfonic acid
PPA: polyphosphoric acid
*2Based on the amount of p-hydroxybenzaldoxime

EXAMPLES 22–30

Experiments were carried out by using p-hydroxybenzaldoxime as a starting material and toluene as a solvent in the presence of various kinds of amides at 100° C. for 6 hrs. The results were as shown in Table 4:

TABLE 4

| Example | Amides*1 (Amounts*2 of addition) | Catalysts (Amounts) | | Conversion (%) | Yield (%) |
|---|---|---|---|---|---|
| 22 | FA (0.2) | $H_2SO_4$ | (9 mole %) | 95 | 88 |
| 23 | FA (0.1) | $H_2SO_4$ | (14 mole %) | 92 | 82 |
| 24 | FA (0.2) | $(COOH)_2$ | (11 mole %) | 99 | 94 |
| 25 | FA (0.2) | $HNO_3$ | (10 mole %) | 98 | 92 |
| 26 | FA (0.2) | HCl | (10 mole %) | 98 | 91 |
| 27 | FA (0.2) | HCOOH | (10 mole %) | 97 | 89 |
| 28 | MFA (0.2) | $H_2SO_4$ | (50 mole %) | 99 | 89 |
| 29 | DMF (0.2) | $H_2SO_4$ | (50 mole %) | 99 | 90 |
| 30 | FA (0.2) | None | | 93 | 87 |

Note:
*1Abbreviations shown in Table 4 means as follows:
FA: formamide
MFA: N—methylformamide
DMF: N,N—dimethylformamide
*2Amount of addition means volume amount (ml) of amide added based on 1 part by weight (g) of p-hydroxybenzaldoxime.

What is claimed is:

1. In a process for producing a nitrile compound from a corresponding aldehyde exhibited by the general formula (I) and a hydroxylamine inorganic acid salt $$R^1CHO \quad (I)$$

or from an aldoxime exhibited by the general formula (II), $$R^2CH=NOH \quad (II)$$

(in the general formulas shown hereinabove, $R^1$ represents an aryl group having 6 to 9 carbon atoms and $R^2$ represents an alkyl or alkenyl group having 1 to 9 carbon atoms or an aryl group having 6 to 9 carbon atoms), a process, wherein water produced in the reaction is azeotropically distilled out of the reaction system with the aid of a solvent which makes an azeotropic mixture with water.

2. A process for producing a nitrile compound according to claim 1, wherein the reaction is carried out in the presence of an amide compound.

3. A process for producing a nitrile compound according to claim 1, wherein $R^1$ and $R^2$ in the general formulas (I) and (II), respectively, are substituted by hydroxyl, nitro, cyano, alkoxyl, alkoxycarbonyl, amido group or halogen atom.

4. A process for producing a nitrile compound according to claim 1, wherein an aldehyde and an aldoxime are p-hydroxybenzaldehyde and p-hydroxybenzaldoxime, respectively, and a nitrile compound obtained is p-cyanophenol.

5. A process for producing a nitrile compound according to claim 2, wherein an amide compound is formamide, N-methylformamide, N,N-dimethylformamide, acetamide, N-methylacetamide, N,N-dimethylacetamide, N-methylpyrrolidone or hexamethylphosphoric triamide.

6. A process for producing a nitrile compound according to claim 2, wherein an amide compound is formamide.

7. A process for producing a nitrile compound according to claim 1, wherein a solvent which makes an azeotropic mixture is benzene, toluene, xylene, chlorobenzene or heptane.

* * * * *